(12) United States Patent
Getzenberg

(10) Patent No.: US 7,531,634 B2
(45) Date of Patent: May 12, 2009

(54) BLADDER MATRIX PROTEIN PEPTIDES AND METHODS OF DETECTION OF BLADDER CANCER

(75) Inventor: Robert H. Getzenberg, Lutherville, MD (US)

(73) Assignee: University of Pittsburgh, Pittsburgh, PA (US)

( * ) Notice: Subject to any disclaimer, the term of this patent is extended or adjusted under 35 U.S.C. 154(b) by 238 days.

(21) Appl. No.: 11/292,278

(22) Filed: Dec. 2, 2005

(65) Prior Publication Data

US 2006/0154311 A1 Jul. 13, 2006

Related U.S. Application Data

(60) Provisional application No. 60/632,646, filed on Dec. 3, 2004.

(51) Int. Cl.
C07K 16/00 (2006.01)
C07K 14/00 (2006.01)

(52) U.S. Cl. .................. 530/387.1; 530/350; 530/391.1; 530/391.3

(58) Field of Classification Search ........................ None
See application file for complete search history.

(56) References Cited

U.S. PATENT DOCUMENTS 6,783,961 B1 8/2004 Edwards et al.
2008/0038264 A1* 2/2008 Bodary et al. ............ 424/139.1

FOREIGN PATENT DOCUMENTS

WO WO0231111 * 4/2002
WO WO03009343 * 11/2003

OTHER PUBLICATIONS

Sequence search result.*
Robert H. Getzenberg, "Nuclear Matrix and Regulation of Gene Expression: Tissue Specificity", Journal of Cellular Biochemistry, 55: 22-31 (1994).
Ronald Berezney et al., "Identification of a Nuclear Protein Matrix", Biochemical & Biophysical Research Communications, vol. 60, No. 4, 1974, pp. 1410-1417.
Edward G. Fey et al., "The Nuclear Matrix: Defining Structural & Functional Roles", Eukaryotic Gene Expression, vol. 1, Issue 2, pp. 127-143 (1991).
Ronald Berezney et al., "Isolation and Characterization of the Nuclear Matrix from Zajdela Ascites Hepatoma Cells", Cancer Research, 29, 3031-3039, Aug. 1979.
Edward G. Fey et al., "Tumor promoters induce a specific morphological signature in the nuclear matrix—intermediate filament scaffold of Madin—Darby canine kidney (MDCK) cell colonies", Proc. Natl. Acad. Sci. USA, vol. 81, pp. 4409-4413, Jul. 1984.
Edward G. Fey et al., "Nuclear matrix proteins reflect cell type of origin in cultured human cells", Proc. Natl. Acad. Sci. USA, vol. 85, pp. 121-125, Jan. 1988.
Noel Weidner et al., "Rapid Communication Localization of Nuclear Matrix Proteins (NMPs) in Multiple Tissue Types with NM-200.4 (An Antibody Strongly Reactive with NMPs Found in Breast Carcinoma)", American Journal of Pathology, vol. 138, No. 6, Jun. 1991, pp. 1293-1298.
Pranab Dey, "Urinary Markers of Bladder Carcinoma", Clinica Chimica Acta 340 (2004) pp. 57-65.
Shahrokh F. Shariat et al., "Urine Detection of Survivin is a Sensitive Marker for the Noninvasive Diagnosis of Bladder Cancer", The Journal of Urology, vol. 171, pp. 626-630, Feb. 2004.
Afina S. Glas et al., "Tumor Markers in the Diagnosis of Primary Bladder Cancer. A Systematic Review", The Journal of Urology, vol. 169, Jun. 2003, pp. 1975-1982.
R.B. Merrifield, "Solid Phase Peptide Synthesis. I. The Synthesis of a Tetrapeptide", Synthesis of a Tetrapeptide, vol. 85, Jul. 20, 1963, pp. 2149-2153.
John Morrow Steward et al., "Solid Phase Peptide Synthesis", pp. 27-64, (1969).
William D. Huse et al., "Generation of a Large Combinatorial Library of the Immunoglobulin Repertoire in Phage Lambda", Science, vol. 246, pp. 1275-1281, Dec. 1989.
Rebecca L. Mullinax et al., "Identification of human antibody fragment clones specific for tetanus toxoid ina bacteriophage λ immunoexpression library", Proc. Natl. Acad. Sci. USA, vol. 87, pp. 8095-8099, Oct. 1990.
E. Diener et al., "Specific Immunosuppression by Immunotoxins Containing Daunomycin", Science, vol. 231, pp. 148-150, Jan. 1986.
John W. Greiner et al., "Recombinant Interferon Enhances Monoclonal Antibody—Targeting of Carcinoma Lesions In Vivo", Science, vol. 235, pp. 895-898, Feb. 1987.
Barbara Wolff et al., "The Use of Monoclonal Anti-$Thy_1$ $IgG_1$ for the Targeting of Liposomes to AKR-A Cells In Vitro and In Vivo", Biochimica et Biophysica Acta, 802 (1984) pp. 259-273.
Harold M. Weintraub, Antisense RNA and DNA, Scientific America, Jan. 1990, pp. 40-46.
Thomas R. Cech, PhD, "Ribozymes and Their Medical Implications", JAMA, Nov. 25, 1988, vol. 260, No. 20, pp. 3030-3034.
Jim Haseloff et al., "Simple RNA enzymes with new and highly specific endoribonuclease activities", Nature, vol. 334, Aug. 18, 1988, pp. 585-591.

(Continued)

Primary Examiner—Larry R. Helms
Assistant Examiner—Lei Yao
(74) Attorney, Agent, or Firm—Stephen A. Bent; Shaun R. Snader; Foley & Lardner LLP

(57) ABSTRACT

Nuclear matrix proteins (NMP) which are characterized by a defined expression in tissue are provided. These NMPs are useful markers in diagnosing and monitoring the stage of malignancy of a cell and treating cell proliferative disorders associated with the NMP. Also provided are substantially purified polypeptides and polynucleotide sequences encoding the NMPs, and particularly, those of BLCA-1, and antibodies thereto.

4 Claims, 6 Drawing Sheets

OTHER PUBLICATIONS

Robert Fraley et al., "New generation liposomes: the engineering of an efficient vehicle for intracellular delivery of nucleic acids", TIBS—Mar. 1981, pp. 77-80.

Edward G. Fey et al., "Epithelial Cytoskeletal Framework and Nuclear Matrix—Intermediate Filament Scaffold: Three-dimensional Organization and Protein Composition", The Journal of Cell Biology, vol. 98, Jun. 1984, pp. 1973-1984.

Robert H. Getzenberg et al., "Identification of Nuclear Matrix Proteins in the Cancer and Normal Rat Prostate", Cancer Research, 51, Dec. 15, 1991, pp. 6514-6520.

Kris Gevaert et al., "New Strategies in High Sensitivity Characterization of Proteins Separated From 1-D or 2-D Gels", Methods in Protein Structure Analysis, 1995, pp. 15-27.

Gisela Brünagel et al., "Identification of Nuclear Matrix Protein Alterations Associated with Human Colon Cancer", Cancer Research 62, Apr. 15, 2002, pp. 2437-2442.

Douglas A. West et al., "Role of Chronic Catheterization in the Development of Bladder Cancer in Patients With Spinal Cord Injury", Adult Urology, 1999, pp. 292-297.

Darwich E. Beiany et al., "Malignant Vesical Tumors Following Spinal Cord Injury", The Journal of Urology, vol. 138, 1987, pp. 1390-1392.

* cited by examiner

SEQUENCE LISTING

<160> NUMBER OF SEQ ID NOS: 11

<210> SEQ ID NO 1
<211> LENGTH: 6
<212> TYPE: PRT
<213> ORGANISM: Homo sapiens

<400> SEQUENCE: 1

Leu Ala Lys Ile Val Leu
 1               5

<210> SEQ ID NO 2
<211> LENGTH: 8
<212> TYPE: PRT
<213> ORGANISM: Homo sapiens

<400> SEQUENCE: 2

Glu Ile Ser Gln Leu Asn Ala Gly
 1               5

<210> SEQ ID NO 3
<211> LENGTH: 8
<212> TYPE: PRT
<213> ORGANISM: Homo sapiens

<400> SEQUENCE: 3

Val Tyr Glu Asp Ile Met Gln Lys
 1               5

<210> SEQ ID NO 4
<211> LENGTH: 12
<212> TYPE: PRT
<213> ORGANISM: Homo sapiens

<400> SEQUENCE: 4

Ser Leu Asp Leu Asp Leu Ile Ile Ala Glu Val Lys
 1               5                  10

<210> SEQ ID NO 5
<211> LENGTH: 8
<212> TYPE: PRT
<213> ORGANISM: Homo sapiens
<220> FEATURE:
<221> NAME/KEY: MOD_RES
<222> LOCATION: (1)
<223> OTHER INFORMATION: variable amino acid

<400> SEQUENCE: 5

Xaa Leu Asp Gln Glu Val Asn Thr
 1               5

<210> SEQ ID NO 6
<211> LENGTH: 10
<212> TYPE: PRT
<213> ORGANISM: Homo sapiens

<400> SEQUENCE: 6

Ala Leu Ile Leu Glu Leu Glu Ile Glu Asn
 1               5                  10

```
<210> SEQ ID NO 7
<211> LENGTH: 9
<212> TYPE: PRT
<213> ORGANISM: Homo sapiens

<400> SEQUENCE: 7

Met Lys Phe Glu Met Glu Gln Tyr Leu
 1               5

<210> SEQ ID NO 8
<211> LENGTH: 11
<212> TYPE: PRT
<213> ORGANISM: Homo sapiens

<400> SEQUENCE: 8

Thr Tyr Glu Glu Lys Ile Asn Lys Gln Gly Lys
 1               5                  10

<210> SEQ ID NO 9
<211> LENGTH: 10
<212> TYPE: PRT
<213> ORGANISM: Homo sapiens

<400> SEQUENCE: 9

Trp Leu Leu Glu Gly Phe Arg Ser Arg Arg
 1               5                  10

<210> SEQ ID NO 10
<211> LENGTH: 10
<212> TYPE: PRT
<213> ORGANISM: Homo sapiens
<220> FEATURE:
<221> NAME/KEY: MOD_RES
<222> LOCATION: (2)
<223> OTHER INFORMATION: variable amino acid

<400> SEQUENCE: 10

Asn Xaa Leu Asp Gln Glu Val Asn Thr Glu
 1               5                  10

<210> SEQ ID NO 11
<211> LENGTH: 10
<212> TYPE: PRT
<213> ORGANISM: Homo sapiens

<400> SEQUENCE: 11

Met Lys Phe Glu Met Glu Gln Tyr Leu Glu
 1               5                  10
```

BLADDER MATRIX PROTEIN PEPTIDES AND METHODS OF DETECTION OF BLADDER CANCER

This application claims benefit of U.S. provisional application Ser. No. 60/632,646, filed Dec. 3, 2004. That application is incorporated herein by reference.

This invention was made with support from the University of Pittsburgh and from NIH/NCI grant CA82522 to the University of Pittsburgh. The United States Government has certain rights to the invention described herein.

BACKGROUND

The present invention relates generally to bladder nuclear matrix proteins, called "NMPs" here, and more specifically to novel nuclear matrix proteins of the bladder which are associated with cell-proliferative disorders.

The early diagnosis of bladder cancer is central to the effective treatment of the disease. Currently, there are no methods available to easily and specifically identify the presence of bladder cancer cells. The prevailing technique for diagnosis of bladder cancer is to identify bladder cancer cells by morphological examination of the cells by a pathologist. A cellular hallmark of the transformed phenotype is abnormal nuclear shape, the presence of multiple nucleoli and altered patterns of chromatin organization. Nuclear structural alterations are so prevalent in cancer cells that they are commonly used as a pathological marker of transformation for many types of cancer. Nuclear shape is determined in part by the nuclear matrix, the dynamic skeleton of the nucleus.

The nuclear matrix is the structural component of the nucleus that determines nuclear morphology, organizes the DNA in a three-dimensional fashion that is tissue specific, and has a central role in the regulation of a number of nuclear processes including the regulation of gene expression. The nuclear matrix plays a central role in the regulation of important cellular processes such as DNA replication and transcription. Getzenberg, *J. Cell Biochem.* 55: 22-31 (1994). The nuclear matrix also forms the framework or scaffolding of the nucleus and consists of the peripheral laminas and pore complexes, an internal ribonucleic protein network, and residual nucleoli. Berezney et al., *Biochem. Biophys. Res. Comm.* 60: 1410 -17 (1974). The nuclear matrix consists of approximately 10% of the nuclear proteins and is virtually devoid of lipids, DNA and histones. Fey et al., *Critical Reviews in Eukaryotic Gene Expression* 1: 127-44 (1991).

A majority of the known NMPs are common to all cell types and physiologic states. A number of NMPs may be unique to certain cell types or states. The composition of NMPs and their structure are altered by mitogenic stimulation and the induction of cellular differentiation. The nuclear matrix contains a number of associated proteins that have been demonstrated to be involved in transformation. While examining hepatoma nuclear matrix proteins, Berezney et al. first showed that the nuclear matrix is altered in transformation. Berezney et al., *Cancer Res.* 39: 3031-39 (1979). Fey and Penman demonstrated that tumor promoters induce a specific morphologic signature in the nuclear matrix-intermediate filament scaffold of kidney cells. Fey et al., *Proc. Nat'l Acad. Sci. USA* 81: 859-66 (1984). Fey and Penman went on to demonstrate that the pattern of NMPs differed between normal and tumorigenic cell lines. Fey et al., *loc. cit.* 85: 121-25 (1989). More recently, an antibody to a nuclear matrix protein, termed NM-200.4, was raised from the breast carcinoma cell line T-47D. Weidner et al., *Am. J. Path.* 138: 1293-98 (1991). This antibody reacts strongly with human breast carcinoma specimens as well as specimens from lung, thyroid, and ovarian cancers, but does not react with normal epithelial cells of similar origin, raising the possibility of the use of certain anti-NMP antibodies as diagnostic tools.

Two urine-based tests that are commercially available are NMP22 and BTA. The reported sensitivity of the NMP22 test ranges between 68.5% and 88.5% while its specificity ranges from 65.2 to 91.3%. See, e.g., Dey, P., *Clin. Chim. Acta* 340:57-65 (2004). The reported sensitivity of the BTA stat test ranges from 57 to 83% and specificity varies from 68 to 72%. Another protein currently being researched for the detection of bladder cancer, survivin, has a high potential specificity at 94%; however, the sensitivity is only 64%. See Shariat et al., *J. Urol.* 171:626-630 (2004). As such, the use of these urine markers in the detection of bladder cancer is limited by their somewhat poor sensitivity and specificity.

Likewise, the current methods applied in the detection of bladder cancer lack the sensitivity required for the detection of low grade tumors. It is very important to detect bladder cancer in the early stages because the 5-year survival rate is 94% when this cancer is detected early at a localized stage. The current "gold standard" to detect bladder cancer is cystoscopy, which is an invasive test that involves inserting a scope into the urethra. Cytology is commonly used but lacks sensitivity. Cytology has a reported specificity of 94% but the sensitivity is only approximately 55%. See Glas et al., *J. Urol.* 169:1975 -1982 (2003). Therefore, there is a great need for a test that is both sensitive and specific that is noninvasive and can easily be sampled over time.

BRIEF DESCRIPTION OF THE FIGURES

A brief description of each figure is provided below.

SUMMARY OF THE INVENTION

Figure 1:
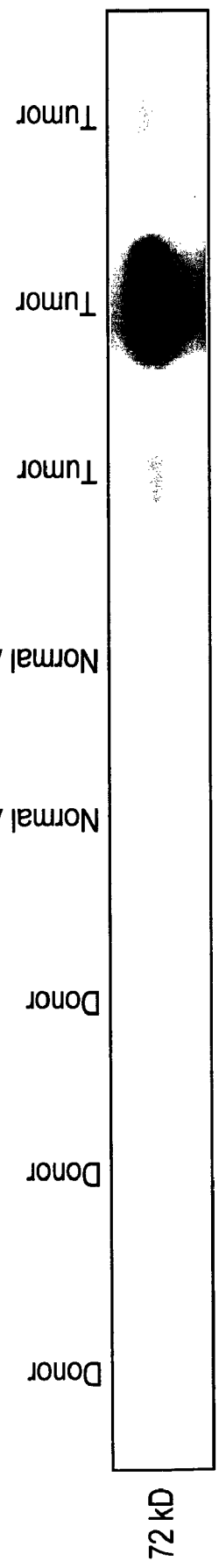
FIG. 1 shows an immunoblot of the nuclear matrix protein BLCA-1 in bladder tissue in which an anti-BLCA-1 antibody was used to detect the protein in tissue from donors without urologic malignancies, in normal adjacent bladder tissue, or in cancerous tissue samples.

In one embodiment, the invention relates to nuclear matrix proteins that are able to differentiate cancerous cells from normal cells, polynucleotide sequences encoding them, and their methods of use. Six proteins, respectively designated BLCA-1, BLCA-2, BLCA-3, BLCA-4, BLCA-5 and BLCA-6, were discovered to be present in all cancerous bladder cells but not present in the normal bladder cells. In addition, three proteins (referred to as BLNL-1, BLNL-2, and BLNL-3) were discovered to be unique to normal bladder tissue. These proteins are useful for diagnosing and producing treatments for cell proliferative disorders of the bladder.

In one embodiment, compositions comprise peptide fragments of BLCA-1. Such fragments include the immunogenic amino acid sequences of SEQ ID NO: 5-9.

In another embodiment, isolated polynucleotides are provided that consist essentially of a nucleic acid sequence encoding an amino acid sequence such as SEQ ID NO: 5-9.

In another embodiment, an isolated or purified antibody specifically binds to a nuclear matrix protein or a fragment thereof, wherein the nuclear matrix protein is BLCA-1 having a molecular weight of about 72 kD and a pI of about 7.70. In one aspect, the antibody is a monoclonal antibody, polyclonal antibody, humanized antibody, or antibody fragment. In another aspect, the antibody is coupled to a therapeutic agent. In one embodiment, the antibody is labeled with a labeling agent such as a radioisotope or paramagnetic isotope, a bioluminenscent compound, a chemiluminescent compound, a fluorescent compound, a metal chelate, an enzyme, or biotin. In another embodiment, the fragment to which the antibody specifically binds is an amino acid sequence of SEQ ID NO: 5-9.

In one embodiment, a method for diagnosing a subject having a cell-proliferative disorder or determining if a subject is at risk of developing a cell-proliferative disorder are provided. The method comprises obtaining a sample from a subject having a cell-proliferative disorder or at risk of developing a cell-proliferative disorder and contacting the sample with the inventive anti-BLCA-1 antibodies wherein a cell-proliferative disorder or risk of a cell-proliferative disorder is indicated by antibody binding to the protein or antigen. In one aspect, the sample is tissue, serum, lavage fluid or urine. In another aspect, the method further comprises contacting the sample with a second antibody that specifically binds to a different immunogenic amino acid sequence. In one aspect, the first antibody and second antibody specifically bind to different fragments having an amino acid sequence selected from the group consisting of SEQ ID NO: 5-9. In another aspect, the second antibody specifically binds to BLCA-4, having a molecular weight of about 37 kD and a pI of about 6.24, or a fragment thereof. In a further aspect, the second antibody specifically binds to a fragment having an amino acid sequence of SEQ ID NO: 2.

In another embodiment, a method for determining a prognosis for a cell proliferative disorder is provided comprising obtaining a sample from a subject having a cell-proliferative disorder or at risk of developing a cell-proliferative disorder and contacting the sample with an anti-BLCA-1 antibody, wherein the prognosis is indicated by the degree of antibody binding to the protein or antigen. In a further embodiment, the antibody specifically binds to a immunogenic amino acid sequence selected from the group consisting of SEQ ID NO: 5-9. In another aspect, the method further comprises contacting the sample with a second antibody that specifically binds to a different immunogenic amino acid sequence. In one aspect, the first antibody and second antibody specifically bind to different fragments having an amino acid sequence selected from the group consisting of SEQ ID NO: 5-9. In another aspect, the second antibody specifically binds to BLCA-4, having a molecular weight of about 37 kD and a pI of about 6.24, or a fragment thereof. In a further aspect, the second antibody specifically binds to a fragment having an amino acid sequence of SEQ ID NO: 2.

In another embodiment, a method for diagnosing a subject having a cell proliferative disorder or determining if a subject is at risk of developing a cell proliferative disorder comprises contacting the nucleic acids of bladder cells of a subject having a cell proliferative disorder or at risk of developing a cell proliferative disorder with the inventive polynucleotides under conditions whereby a hybridization complex is formed, and detecting the hybridization complex, wherein the cell proliferative disorder or risk of the cell proliferative disorder is indicated by the presence of the hybridization complex. In one aspect, the method utilizes a polynucleotide detectably labeled with a label such as a radioisotope, a bioluminenscent compound, a chemiluminescent compound, a fluorescent compound, a metal chelate, and an enzyme.

In one embodiment, a method for diagnosing a subject having a cell proliferative disorder or determining if a subject is at risk of developing a cell proliferative disorder comprises obtaining a sample comprising nucleic acids of cells of a subject having a cell proliferative disorder or at risk of developing a cell proliferative disorder, amplifying from the sample a target polynucleotide having a sequence of the inventive polynucleotides or a fragment thereof, and detecting the amplified target polynucleotide or fragment, wherein the cell proliferative disorder or risk of a cell proliferative disorder is indicated by the presence of the amplified target polynucleotide or fragment.

Other objects, features and advantages of the present invention will become apparent from the following detailed description. The detailed description and specific examples, while indicating preferred embodiments, are given for illustration only since various changes and modifications within the spirit and scope of the invention will become apparent to those skilled in the art from this detailed description. Further, the examples demonstrate the principle of the invention and cannot be expected to specifically illustrate the application of this invention to all the examples where it will be obviously useful to those skilled in the prior art.

DETAILED DESCRIPTION

Nuclear matrix proteins which are present in normal cells but absent in cancerous cells, or which are absent in normal cells but present in cancerous cells, act as useful markers of disease. In particular, the proteins BLNL-1, BLNL-2 and BLNL-3 are present in normal bladder cells but absent in cancerous bladder cells. In addition, the proteins BLCA-1, BLCA-2, BLCA-3, BLCA-4, BLCA-5 and BLCA-6 are present in cancerous bladder cells. Moreover, a fragment of a nuclear matrix protein is presented, wherein the nuclear matrix protein is BLCA-1 having a molecular weight of about 72 kD and a pI of about 7.70, and wherein the fragment is an amino acid sequence selected from the group consisting of XLDQEVNT (SEQ ID NO: 5), ALILELEIEN (SEQ ID NO: 6), MKFEMEQYL (SEQ ID NO: 7), TYEEKINKQGK (SEQ ID NO: 8), and WLLEGFRSRR (SEQ ID NO: 9).

In another embodiment, a purified polynucleotide sequence is presented encoding the above identified NMPs or NMP fragments of the preceding embodiment. In particular, polynucleotides encoding a fragment of a nuclear matrix protein, wherein the nuclear matrix protein is BLCA-1 having a molecular weight of about 72 kD and a pI of about 7.70, and wherein the fragment is an amino acid sequence selected from the group consisting of SEQ ID NO: 5-9. Another embodiment is a purified polynucleotide sequence which hybridizes to the polynucleotide sequence encoding the above-mentioned NMPs or NMP fragments.

Another embodiment is a recombinant expression vector containing any of the amino acid sequences of SEQ ID NO: 5-9. In one aspect, the recombinant expression vector is a plasmid. The plasmid can include an origin of replication (replicons) for a particular host cell. Various prokaryotic replicons are known to those skilled in the art, and function to direct autonomous replication and maintenance of a recombinant molecule in a prokaryotic host cell. See, e.g., Sambrook J. and D. W. Russell (2001) *Molecular Cloning A Laboratory Manual,* 3d ed., Cold Spring Harbor Laboratory Press, Cold Spring Harbor, N.Y., and Ausubel et al. (1989) *Current Protocols In Molecular Biology,* John Wiley & Sons, Brooklyn, N.Y. Likewise, the recombinant expression vector can include promoters, introns, and termination sequences. See Sambrook et al., supra. Additionally, the recombinant expression vector can be a virus. Exemplary viral vectors can be RNA viruses such as retroviruses. In another aspect, the recombinant expression vector is delivered using a liposome. In a further aspect, the liposome is target-specific and can be targeted with, for example, an antibody or ligand.

Another embodiment is a host cell transformed with a polynucleotide sequence encoding the above-mentioned NMPs or NMP fragments. Transformation of a host cell with recombinant DNA can be carried out by conventional techniques. Where the host is prokaryotic, such as *E. coli*, competent cells which are capable of DNA uptake can be prepared from cells harvested after the exponential growth phase and subsequently treated by the $CaCl_2$ method. Alternatively, $MgCl_2$ or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the NMPs of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. Gluzman (ed.), *Eukaryotic Viral Vectors,* Cold Spring Harbor Laboratory, 1982.

Isolation and purification of the NMPs or NMP fragments expressed by a transformed host can be carried out by conventional means including preparative chromatography and immunological separations involving monoclonal or polyclonal antibodies.

In one embodiment, the NMP polypeptide or fragments can be used to prepare antibodies. These antibodies specifically bind a fragment of a nuclear matrix protein, wherein the nuclear matrix protein is BLCA-1 having a molecular weight of about 72 kD and a pI of about 7.70, and wherein the fragment is an amino acid sequence selected from the group consisting of SEQ ID NO: 5-9.

Another embodiment is an antibody which binds to the above-mentioned NMPs or NMP fragments. The antibody can be polyclonal or monoclonal. The antibody can also be a humanized antibody or an antibody fragment. Using the NMPs, antibodies can be prepared that are capable of differentiating between cancerous bladder tissue and normal bladder tissue. Furthermore, antibodies which specifically bind the NMPs can detect individuals at risk of developing bladder cancer before morphological change is even visible in tissue samples.

In an additional embodiment, antibodies which specifically bind to a nuclear matrix protein or an antigen thereof is advantageous over prior art antibodies for bladder cancer because the NMPs of the present invention that are associated with bladder cancer cells (i.e., BLCA-1 through 6) are believed not to be present in subjects afflicted with cystitis who do not have bladder cancer. As a result, cystitis patients who do not suffer from bladder cancer are not falsely indicated as having cancer when antibodies according to the present invention are used. This is an important improvement over the prior art diagnostic methods. In one aspect, an antibody specifically binds to BLCA-1. In a further aspect, an antibody specifically binds to a BLCA-1 fragment such as the amino acid sequences of SEQ ID NO: 5-9. In another aspect, an antibody specifically binds to BLCA-4. In yet another aspect, an antibody specifically binds to an antigen including the amino acid sequence of SEQ ID NO: 2.

Another embodiment is a method for detecting a cell proliferative disorder in a subject or for detecting individuals at risk of developing a cell proliferative disorder comprising contacting a cellular component from the subject with an antibody or nucleic acid probe which binds to a cellular component associated with the cell proliferative disorder. In one aspect, the cellular component is taken from the subject's bladder and is preferably a nucleic acid. In a further aspect, the nucleic acid is DNA encoding the above-mentioned NMPs or NMP fragments. In another aspect, the nucleic acid is RNA. In yet another aspect, the cellular component is the above-mentioned NMPs or NMP protein fragments. The NMP or NMP fragment can be collected from tissue, serum, lavage fluid or voided urine samples. If the cellular component is an NMP or NMP fragment, then an antibody is used which specifically binds to the NMP or NMP fragment. As noted above, the antibody can be monoclonal or polyclonal. The antibody can also be a humanized antibody or an antibody fragment.

In one embodiment, a nucleic acid probe specifically hybridizes to the above-mentioned cellular component. When the reagent is a nucleic acid probe, it can be detectably labeled. Such labels include a radioisotope, a bioluminescent compound, a chemiluminescent compound, a fluorescent compound, a metal chelate and an enzyme.

One embodiment is a method for diagnosing a subject having a cell-proliferative disorder or determining if a subject is at risk of developing a cell-proliferative disorder, comprising obtaining a sample comprising nucleic acids of cells of a subject having a cell-proliferative disorder or at risk of developing a cell-proliferative disorder, amplifying from the sample a target polynucleotide having a sequence of the inventive polynucleotides or a fragments, and detecting the amplified target polynucleotide or fragment, wherein bladder cancer or risk of bladder cancer is indicated by the presence of the amplified target polynucleotide or fragment. In one aspect, the amplification step is performed by an amplification technique such as polymerase chain reaction, ligase chain reaction, loop-mediated isothermal amplification, nucleic acid sequence based amplification, self-sustained sequence replication, strand displacement amplification, and transcription mediated amplification.

Another embodiment is a method for determining a prognosis for a cell proliferative disorder comprising obtaining a sample from a subject having a cell-proliferative disorder or at risk of developing a cell-proliferative disorder and contacting the sample with an antibody that specifically binds to an NMP, such as BLCA-1, or fragment of an NMP, wherein the prognosis is indicated by the degree of antibody binding to the protein or antigen. In a further embodiment, the antibody specifically binds to a immunogenic amino acid sequence selected from the group consisting of SEQ ID NO: 5-9. In another aspect, the method further comprises contacting the sample with a second antibody that specifically binds to a different immunogenic amino acid sequence. In one aspect, the first antibody and second antibody specifically bind to different fragments having an amino acid sequence selected from the group consisting of SEQ ID NO: 5-9. In another aspect, the second antibody specifically binds to BLCA-4, having a molecular weight of about 37 kD and a pI of about 6.24, or a fragment thereof. In a further aspect, the second antibody specifically binds to a fragment having an amino acid sequence of SEQ ID NO: 2.

Another embodiment is a method of treating a cell proliferative disorder associated with a protein selected from the group consisting of BLCA-1, BLCA-2, BLCA-3, BLCA-4, BLCA-5, BLCA-6, BLNL-1, BLNL-2, and BLNL-3, comprising administering to a subject with the disorder a therapeutically effective amount of an antisense polynucleotide sequence that blocks the sequences encoding the above-mentioned NMPs. Preferably, the antisense polynucleotide sequence that blocks sequences encoding the amino acid sequences of SEQ ID NO: 5-9. In one aspect, the treatment is designed to block the expression of one or more NMPs which give rise to the cell proliferative disorder.

In another embodiment, a method of treating a cell proliferative disorder comprises, instead of using an antisense polynucleotide sequence, a polynucleotide sequence which encodes one of the above-mentioned NMPs. In this embodiment, the treatment is designed to provide the subject with one or more NMPs that prevent or ameliorate the cell proliferative disorder.

In another method of treatment, an antibody is administered to the subject which is capable of blocking the function of one or more of the above NMPs.

Another embodiment is a method of gene therapy, comprising introducing into the cells of a host subject an expression vector comprising a polynucleotide sequence encoding one or more of the above-mentioned NMPs or NMP fragments. In one aspect, the NMP fragment is selected from the amino acid sequences SEQ ID NO: 5-9. In another aspect, the expression vector is introduced into the cells of the host subject ex vivo, yielding transformed cells, and the transformed cells then are reintroduced into the subject. An expression vector that can be used for this purpose is an RNA virus, such as a retrovirus.

Another embodiment is a method for identifying a composition which blocks or enhances the function of a bladder cell NMP comprising incubating NMP-containing bladder cells with a test composition under conditions that allow the bladder cells and test composition to interact, and then measuring whether the test composition blocks or enhances the function of the bladder cell NMP.

Another embodiment is a kit for detecting a cell-proliferative disorder of the bladder comprising a nucleic acid probe that binds to a polynucleotide sequence encoding one of the above-mentioned NMPs. Preferably, the probe is labeled for ease of detection with a label as described above. In one aspect, the kit comprises an antibody which specifically binds to one of the above-mentioned NMPs or NMP fragments. In a further aspect, the antibody specifically binds to a NMP fragment selected from the amino acid sequences SEQ ID NO: 5-9. In another aspect, the kit comprises one or more oligonucleotide primers that permit amplification of a target polynucleotide sequence encoding one of the above-mentioned NMPs, for example, by polymerase chain reaction (PCR) amplification.

The NMPs can be fragments and conservatively substituted variants thereof. Minor modifications of the NMP primary amino acid sequence can result in proteins which have substantially equivalent activity as compared to the NMP polypeptide described herein (i.e. bioequivalent). Such modifications can be deliberate, as by site-directed mutagenesis, or can be spontaneous. Such modifications include deletion of non-essential amino acids. All of the polypeptides produced by these modifications are included herein as long as the biological activity of the native NMP still exists. In addition, deletion of one or more amino acids can also result in a modification of the structure of the resultant molecule without significantly altering its biological activity. This can lead to the development of a smaller active molecule.

The term "conservative substitution" refers to the replacement of an amino acid residue by a structurally similar residue. Examples of conservative substitutions include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like.

Peptides can be synthesized by the well known solid phase peptide synthesis methods described, for example, by Merrifield, *J. Am. Chem. Soc.* 85: 2149 (1962), and by Stewart and Young, *Solid Phase Peptides Synthesis*, pages 27-62, Freeman Publ., 1969.

The present polyclonal and monoclonal antibodies are immunoreactive with the NMPs or immunogenic fragments of the NMPs. If desired, polyclonal antibodies can be further purified, for example, by binding to and elution from a matrix to which NMP polypeptide is bound or by utilizing common nuclear matrix proteins to selectively remove non-specific antibodies. Antibody which consists essentially of pooled monoclonal antibodies with different epitopic specificities, as well as distinct monoclonal antibody preparations are provided. The term "antibody," as used herein, includes intact molecules as well as fragments thereof, such as Fab and $F(ab')_2$ fragments, which are functionally capable of binding an epitopic determinant of an NMP. These polyclonal and monoclonal antibodies can also be humanized antibodies. In one aspect, it is possible to replace all or part of the constant region of these immunoglobulins by all or part of a constant region of a human antibody. For example the $C_H2$ and/or $C_H3$ domains of the immunoglobulin could be replaced by the $C_H2$ and/or $C_H3$ domains of the IgG γ3 human immunoglobulin. In such humanized antibodies it is also possible to replace a part of the variable sequence, namely one or more of the framework residues which do not intervene in the binding site by human framework residues, or by a part of a human antibody.

A method for the identification and isolation of antibody binding domains which exhibit binding with NMP is the bacteriophage λ vector system. This vector system has been used to express a combinatorial library of Fab fragments from the mouse antibody repertoire in *Escherichia coli*, see Huse et al., *Science* 246: 1275-81 (1989), and from the human antibody repertoire. Mullinax et al., *Proc. Nat'l Acad. Sci. USA* 87: 8095-99 (1990).

As used herein, the term "cell-proliferative disorder" refers to malignant as well as non-malignant (or benign) disorders. The cells comprising these proliferative disorders often appear morphologically and genotypically to differ from the surrounding normal tissue. As noted above, cell-proliferative disorders can be associated, for example, with expression or absence of expression of the NMPs of the invention. Expression of an NMP at an inappropriate time during the cell cycle or in an incorrect cell type can result in a cell-proliferative disorder. This term also refers to hyperplastic disorders of the bladder. The NMP-encoding polynucleotide in the form of an antisense polynucleotide is useful in treating hyperplasia and malignancies of the bladder. When the cell-proliferative disorder is associated with NMP expression, (e.g., BLCA-1, 2, 3, 4, 5 and/or 6), an antisense NMP polynucleotide sequence or NMP binding antibody can be introduced into the bladder cells to block the expression and/or function of the NMP. Alternatively, when the cell proliferative disorder is associated with under-expression or expression of a mutant NMP polypeptide (e.g., BLNL 1-3), a polynucleotide sequence encoding the missing or under-expressed NMP can be introduced into the cell.

In one embodiment, an antibody or nucleic acid probe specific for an NMP can detect the presence of the NMP polypeptide (in the case of an antibody probe) or polynucleotide (in the case of the nucleic acid probe) in biological fluids or tissues. Oligonucleotide primers based on any coding sequence region in the NMP sequence are useful for amplifying DNA or RNA, for example by PCR. Any specimen containing a detectable amount of antigen can be used. On one hand, tissue can be taken from the bladder. On the other hand, biological fluids which may contain bladder cells or cellular components may be used. In one aspect, the biological fluid is serum, lavage fluid or voided urine.

The term "subject" refers to mammals, such as humans and domestic companion animals.

In other embodiments, the methods consist of coupling an antibody or probe to low molecular weight haptens. These haptens can then be specifically detected by means of a second reaction. For example, it is common to use such haptens as biotin, which reacts with avidin, or dinitrophenol, pyridoxal, and fluorescein, which can react with specific antihapten antibodies. More specifically, the antibodies or polynucleotide sequences of the invention can be labeled with a labeling agent such as a radioisotope or paramagnetic isotope, a bioluminescent compound, a chemiluminescent compound, a fluorescent compound, a metal chelate (i.e., copper or gold), an enzyme, and biotin.

The method for detecting a cell expressing a particular NMP of the invention or a cell-proliferative disorder associated with an NMP, described above, can be utilized for detection of residual bladder cancer or other malignancies or benign hyperplasia conditions in a subject in a state of clinical remission. Additionally, the method for detecting NMP polypeptide in cells is useful for detecting a cell-proliferative disorder by identifying cells expressing specific NMPs in comparison with NMPs expressed in normal cells. In one aspect, NMP expression can be identified in a cell and the appropriate course of treatment can be employed (e.g., NMP-encoding or antisense gene therapy, as well as conventional chemotherapy). Since the expression pattern of the NMPs of the invention vary with the stage of malignancy of a cell, a sample can be screened with a panel of NMP-specific reagents (e.g., nucleic acid probes or antibodies to NMPs) to detect NMP expression and diagnose the stage of malignancy of the cell. In one aspect, BLCA-1, and fragments thereof, can be used to diagnose the stage of malignancy of the cell. In one aspect, the sample is tissue, serum, lavage fluid or urine. In one aspect, the sample is screened with one or more antibodies which specifically bind to BLCA-1 or a fragment of BLCA-1 selected from the amino acid sequences SEQ ID NO: 5-9. In another aspect, the method further comprises contacting the sample with a second antibody that specifically binds to a different immunogenic amino acid sequence. In one aspect, the first antibody and second antibody specifically bind to different fragments having an amino acid sequence selected from the group consisting of SEQ ID NO: 5-9. In another aspect, the second antibody specifically binds to BLCA-4, having a molecular weight of about 37 kD and a pI of about 6.24, or a fragment thereof. In a further aspect, the second antibody specifically binds to a fragment having an amino acid sequence of SEQ ID NO: 2.

The provided monoclonal antibodies can be used in immunoassays in a liquid phase or bound to a solid phase carrier. In one aspect, the monoclonal antibodies in these immunoassays can be detectably labeled. Examples of types of immunoassays include competitive and non-competitive immunoassays in either a direct or indirect format. Examples of such immunoassays are the radioimmunoassay (RIA) and the sandwich (immunometric) assay. Detection of the antigens using the monoclonal antibodies of the invention can be performed utilizing immunoassays which are run in either the forward, reverse, or simultaneous modes, including immunohistochemical assays on physiological samples. Alternatively, an antibody of the invention can be used to detect NMPs present in electrophoretically dispersed gel protocols such as Western blots and two-dimensional gels.

In another aspect, an antibody of the invention can be used to detect NMPs present in samples in enzyme-linked immunosorbent assay (ELISA). Direct, indirect or sandwich ELISA assays can be performed with an inventive antibody.

Generally, the direct ELISA uses the method of directly labeling the antibody itself. Microwell plates are coated with a sample containing the target antigen, and the binding of labeled antibody is quantitated by a calorimetric, chemiluminescent, or fluorescent end-point.

The indirect ELISA utilizes an unlabeled primary antibody in conjunction with a labeled secondary antibody. Since the labeled secondary antibody is directed against all antibodies of a given species (e.g., anti-mouse), it can be used with a wide variety of primary antibodies (e.g., all mouse monoclonal antibodies). The use of secondary antibody also provides a step for signal amplification, increasing the overall sensitivity of the assay.

In a sandwich ELISA, one antibody (the "capture" antibody) is purified and bound to a solid phase. Antigen is then added and allowed to complex with the bound antibody. Unbound antigen are then removed with a wash, and a labeled second antibody (the "detection" antibody) is allowed to bind to the antigen, thus completing the "sandwich." The assay is then quantitated by measuring the amount of labeled second antibody bound to the matrix. Monoclonal antibody combinations useful in a sandwich ELISA must be qualified at "matched pairs," meaning that they can recognize separate epitopes on the antigen. In particular, such epitopes of BLCA-1 can selected from, among others, the amino acid sequences SEQ ID NO: 5-9.

Specific ELISA protocols and experimental techniques are well known and my be found, for example, in Ausubel et al., *Current Protocols In Molecular Biology* (5th Ed.), John Wiley & Sons, New York, N.Y. (2002) or J. R. Crowther, *The ELISA Guidebook: Methods In Molecular Biology* (vol. 149), Humana Press, Totowa, N.J. (2001).

In another embodiment, the sample subjected to an ELISA assay is a biological fluid or bladder tissue sample. Preferably, the biological fluid is voided urine from a subject having bladder cancer or a subject at risk of developing bladder cancer.

The monoclonal antibodies of the invention can be bound to many different carriers and used to detect the presence of NMP. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention.

In performing the assays it may be desirable to include certain "blockers" in the incubation medium (usually added with the labeled soluble antibody). The "blockers" are added to assure that non-specific proteins, proteases, or anti-heterophilic immunoglobulins to anti-NMP immunoglobulins present in the experimental sample do not cross-link or destroy the antibodies on the solid phase support, or the radiolabeled indicator antibody, to yield false positive or false negative results. The selection of "blockers" therefore can increase the specificity of the assays described in the present invention.

It has been found that a number of nonrelevant (i.e., non-specific) antibodies of the same class or subclass (isotype) as those used in the assays (e.g., IgG1, IgG2a, IgM, etc.) can be used as "blockers." The "blockers" are used at a level high enough to maintain the proper sensitivity yet inhibit any unwanted interference by mutually occurring cross reactive proteins in the specimen (normally 1-100 μg/μl).

The term "epitope," as used herein, refers to any determinant capable of specific interaction with the monoclonal antibodies of the invention. Epitopic determinants usually comprise chemically active surface groupings of molecules such as amino acids or sugar side chains and usually have specific three dimensional structural characteristics, as well as specific charge characteristics.

In one embodiment, monoclonal antibodies are used in methods for the in vivo detection of antigen. In one aspect, the detectably labeled monoclonal antibody is given in a dose which is diagnostically effective. The term "diagnostically effective" means that the amount of detectably labeled monoclonal antibody is administered in sufficient quantity to enable detection of the site having the NMP antigen for which the monoclonal antibody is specific.

The dosage of detectably labeled monoclonal antibody for in vivo diagnosis can vary with such factors as age, sex, and extent of disease of the individual. The dosage of monoclonal antibody can vary from about 0.001 mg/m$^2$, to about 500 mg/m$^2$, preferably 0.1 mg/m$^2$ to about 200 mg/m$^2$, most preferably about 0.1 mg/m$^2$ to about 10 mg/m$^2$. Such dosages can vary, for example, depending on whether multiple injections are given, tumor burden, and other factors.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that the half-life of the radioisotope be long enough so that it is detectable at the time of maximum uptake by the target, but short enough so that deleterious radiation with respect to the host is minimized. For example, a radioisotope used for in vivo imaging will lack a particle emission, but produce a large number of photons in the 140-250 keV range, which may be readily detected by conventional gamma cameras.

For in vivo diagnosis, radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr and $^{201}$Tl.

Monoclonal antibodies can also be labeled with a paramagnetic isotope for purposes of in vivo diagnosis, as in magnetic resonance imaging (MRI) or electron spin resonance (ESR). In general, any conventional method for visualizing diagnostic imaging can be utilized. For example, gamma and positron emitting radioisotopes can be used for camera imaging and paramagnetic isotopes can be used for MRI. Elements which are particularly useful in such techniques include $^{157}$Gd, $^{55}$Mn, $^{162}$Dy, $^{52}$Cr, and $^{56}$Fe.

In one embodiment, a method uses monoclonal antibodies to monitor the course of amelioration of an NMP-associated cell-proliferative disorder. By measuring the increase or decrease in the number of cells expressing a NMP or changes in NMP present in various body fluids, such as ejaculate or urine, such methods permit the determination of whether a particular therapeutic regimen aimed at ameliorating the disorder is effective.

In another embodiment, the methods comprise the use of monoclonal antibodies alone or in combination with effector cells, see Douillard et al., *Hybridoma* 5 (Supp. 1): S139 (1986), for immunotherapy in an animal having a cell proliferative disorder which expresses NMP polypeptide with epitopes reactive with the monoclonal antibodies of the invention.

When used for immunotherapy, the monoclonal antibodies can be unlabeled or attached to a therapeutic agent. These agents can be coupled either directly or indirectly to the monoclonal antibodies of the invention. One example of indirect coupling is by use of a spacer moiety. These spacer moieties, in turn, can be either insoluble or soluble, see Diener et al., *Science* 231: 148 (1986), and can be selected to enable drug release from the monoclonal antibody molecule at the target site. Examples of therapeutic agents which can be coupled to the monoclonal antibodies of the invention for immunotherapy are drugs, radioisotopes, lectins, and toxins.

Drugs which can be conjugated to monoclonal antibodies include non-proteinaceous as well as proteinaceous drugs. The terms "non-proteinaceous drugs" refer to compounds which are classically referred to as drugs, for example, mitomycin C, daunorubicin, vinblastine, and others compounds that are used as well to treat cancer.

Proteinaceous drugs which can be joined to monoclonal antibodies include immunomodulators and other biological response modifiers. The term "biological response modifiers" refers to substances which are involved in modifying the immune response in such manner as to enhance the destruction of an NMP-associated tumor. Examples of immune response modifiers include such compounds as lymphokines. Lymphokines include tumor necrosis factor, the interleukins, lymphotoxin, macrophage activating factor, migration inhibition factor, colony stimulating factor, and interferons. Interferons include alpha-interferon, beta-interferon and gamma-interferon and their subtypes.

When using radioisotopically conjugated monoclonal antibodies for immunotherapy certain isotopes may be more preferable than others depending on such factors as tumor cell distribution as well as isotope stability and emission. If desired, the tumor cell distribution can be evaluated by the in vivo diagnostic techniques described above. Depending on the cell proliferative disease some emitters may be preferable to others. In one embodiment, alpha and beta particle-emitting radioisotopes can be used for immunotherapy. For example, if an animal has solid tumor foci a high energy beta emitter capable of penetrating several millimeters of tissue, such as $^{90}$Y, may be preferable. On the other hand, if the cell proliferative disorder consists of simple target cells, as in the case of leukemia, a short range, high energy alpha emitter, such as $^{212}$Bi, may be preferable. Examples of radioisotopes which can be bound to the monoclonal antibodies of the invention for therapeutic purposes are $^{125}$I, $^{131}$I $^{90}$Y, $^{67}$Cu, $^{212}$Bi, $^{211}$At, $^{212}$Pb, $^{47}$SC, $^{109}$Pd, $^{65}$Zn, and $^{188}$Re.

Lectins are proteins, usually isolated from plant material, which bind to specific sugar moieties. Many lectins can agglutinate cells and stimulate lymphocytes. Ricin is a toxic lectin which has been used immunotherapeutically. The alpha-peptide chain of ricin, which is responsible for toxicity, can bind to the antibody of the invention to enable site specific delivery of the toxic effect.

Toxins are poisonous substances produced by plants, animals, or microorganisms, that, in sufficient dose, are often lethal. Diphtheria toxin is a substance produced by *Corynebacterium diphtheria* which can be used therapeutically. This toxin consists of an alpha and beta subunit which under proper conditions can be separated. The toxic A component can be bound to an antibody and used for site specific delivery to a NMP bearing cell.

Monoclonal antibodies also can be used in combination with alpha-interferon. This treatment modality enhances monoclonal antibody targeting of carcinomas by increasing the expression of monoclonal antibody reactive antigen by the carcinoma cells. Greiner et al., *Science* 235: 895 (1987). Alternatively, the monoclonal antibody of the invention can be used, for example, in combination with gamma-interferon to thereby activate and increase the expression of Fc receptors by effector cells which, in turn, results in an enhanced binding of the monoclonal antibody to the effector cell and killing of target tumor cells.

It is also possible to utilize liposomes with monoclonal antibodies captured within the liposomal membrane. When so modified, liposomes specifically deliver the liposome to the tumor expressing NMP. These liposomes can contain, in addition to the monoclonal antibody, immunotherapeutic agents, such as those described above, which would then be released at the tumor site. Wolff et al., *Biochemical et Biophysical Acta* 802: 259 (1984).

The dosage ranges for the administration of monoclonal antibodies are those large enough to produce the desired effect in which the symptoms of the malignant disease are ameliorated. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any complication. Dosage can vary from about 0.1 mg/kg to about 2000 mg/kg, preferably about 0.1 mg/kg to about 500 mg/kg, in one or more dose administrations daily, for one or several days. Generally, when the monoclonal antibodies of the invention are administered conjugated with therapeutic agents, lower dosages, comparable to those used for in vivo diagnostic imaging, can be used.

The monoclonal antibodies of the invention can be administered parenterally by injection or by gradual perfusion over time. The monoclonal antibodies of the invention can be administered intravenously, intraperitoneally, intramuscularly, subcutaneously, intracavity, or transdermally, alone or in combination with effector cells.

In another embodiment, a method for treating a subject with an NMP-associated cell-proliferative disorder using an NMP nucleotide sequence is provided. An NMP nucleotide sequence encoding a suppressor polypeptide can be under-expressed as compared to expression in a normal cell. As such, it is possible to design appropriate therapeutic or diagnostic techniques directed to this sequence. Thus, where a cell-proliferative disorder is associated with the expression of an NMP associated with malignancy, nucleic acid sequences that interfere with NMP expression at the translational level can be used. This approach utilizes, for example, antisense nucleic acid and ribozymes to block translation of a specific NMP mRNA, either by masking that mRNA with an antisense nucleic acid or by cleaving it with a ribozyme. In cases when a cell proliferative disorder or abnormal cell phenotype is associated with the under-expression of NMP suppressor for example, nucleic acid sequences encoding NMP (sense) could be administered to the subject with the disorder.

Antisense nucleic acids are DNA or RNA molecules that are complementary to at least a portion of a specific mRNA molecule. Weintaub, *Scientific American,* 262: 40 (1990). Antisense oligomers can comprise about 15 nucleotides. Oligomers about this size are easily synthesized and likely to be expressed when introduced into the target NMP-producing cell.

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it. Cech, *J. Amer. Med. Assn.* 260: 3030 (1988). A major advantage of this approach is that, because they are sequence-specific, only mRNAs with particular sequences are inactivated.

There are two basic types of ribozymes namely, tetrahymena-type (Hasselhoff, *Nature,* 334:585, 1988) and "hammerhead"-type. Tetrahymena-type ribozymes recognize sequences which are four bases in length, while "hammerhead"-type ribozymes recognize base sequences 11-18 bases in length. The longer the recognition sequence, the greater the likelihood that that sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

In another embodiment, methods are provided for gene therapy for the treatment of cell proliferative disorders mediated by NMP. Gene therapy modalities require introduction of the appropriate NMP polynucleotide sequence (antisense or encoding strand) into cells of subjects having the proliferative disorder. Delivery of antisense NMP polynucleotides can be achieved using a recombinant expression vector such as a viral vector or a liposome. Disorders associated with under-expression of an NMP or expression of a cancer-associated NMP can be treated using gene therapy with the encoding or antisense nucleotide sequences, respectively.

Various viral vectors which can be used for gene therapy include adenovirus, herpes virus, vaccinia, or any RNA virus such as a retrovirus. In one aspect, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. Such retroviral vectors include, but are not limited to, Bovine Immunodeficiency Virus (BIV), Equine Infective Anaemia Virus (EIAV), Feline Immunodeficiency Virus (FIV), Human Immunodeficiency Virus (HIV), and Simian Foamy Virus (SFV, also known as Human Foamy Virus). All of these vectors can transfer or incorporate a gene for a selectable marker so that transduced cells can be identified and generated. By inserting an NMP sequence of interest into the viral vector along with another gene which encodes the ligand for a receptor on a specific target cell, for example, the vector is rendered target specific. Retroviral vectors can be made target specific by inserting, for example, a polynucleotide encoding a sugar, a glycolipid, or a protein. In one aspect, targeting is accomplished by using an antibody to target the retroviral vector.

Since recombinant retroviruses are defective in one or more genes, they require assistance in order to produce infectious vector particles. Helper cell lines possess deletions of the packaging signal include but are not limited to Ψ2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env by conventional calcium phosphate transfection. These cells are then transfected with the vector plasmid containing the genes of interest. The resulting cells release the retroviral vector into the culture medium.

Other targeted delivery systems for NMP antisense polynucleotides include macromolecule complexes, nanocapsules, microspheres, beads, and lipid-based systems including oil-in-water emulsions, micelles, mixed micelles, and liposomes. Liposomes are artificial membrane vesicles which are useful as delivery vehicles in vitro and in vivo. It has been shown that large unilamellar vesicles (ULV), which range in size from 0.2-4.0 μm can encapsulate a substantial percentage of an aqueous buffer containing large macromolecules. RNA, DNA and intact virions can be encapsulated within the aqueous interior and be delivered to cells in a biologically active form. Fraley et al., *Trends Biochem. Sci.* 6: 77 (1981).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidyiserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system can be modified in a variety of ways. In the case of a hyposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

In one embodiment, the compounds bound to the surface of the targeted delivery system are ligands and receptors which will allow the targeted delivery system to find and "home in" on the desired cells. A ligand can be any compound of interest which binds to another compound, such as a receptor.

Surface membrane proteins which bind to specific effector molecules are referred to as receptors. In one aspect, antibodies used herein are preferred receptors. Antibodies can be used to target liposomes to specific cell-surface ligands, such as NMPs. In another aspect, the target tissue is bladder tissue. A number of procedures can be used to covalently attach either polyclonal or monoclonal antibodies to a liposome bilayer. Antibody-targeted liposomes can include monoclonal or polygonal antibodies or fragments thereof such as Fab, or F(ab')$_2$, as long as they bind efficiently to an the antigenic epitope on the target cells.

Preparations for parenteral administration include sterile aqueous or nonaqueous solutions, suspensions, and emulsions. Examples of non aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such an those based on Ringer's dextrose), and the like. Preservatives and other additives may also be present such as, for example, antimicrobials, anti-oxidants, chelating agents and inert gases and the like.

In another embodiment, a method for preparing a medicament or pharmaceutical composition is provided comprising the polynucleotides or the monoclonal antibodies of the invention, the medicament being used for therapy of NMP associated cell proliferative disorders.

The following examples are given to illustrate the present invention. It should be understood, however, that the invention is not to be limited to the specific conditions or details described in these examples. Throughout the specification, any and all references to a publicly available document, including a U.S. patent, are specifically incorporated by reference in their entirety.

EXAMPLES

Tissue Selection

Normal and tumor bladder tissue samples were obtained from patients undergoing surgery for bladder cancer at the University of Pittsburgh Medical Center. Normal bladders were obtained from the Center for Organ Recovery and Education (CORE) via Dr. Michael J. Becich, Department of Pathology, University of Pittsburgh. These bladders provide the opportunity to study nuclear matrix composition and staining in the normal organ which were compared with alterations that occur during transformation from normal to tumor. Samples were only utilized that could clearly be identified by the pathologist as containing approximately pure populations of the stated cell type.

Nuclear Matrix Preparation

The nuclear matrix proteins were isolated from the bladder tissue and tumors selected above as taught in Fey, et al., *J. Cell Biol.*, 98:1973-1984, 1988 and Getzenberg, et al., *Cancer Res.*, 51:6514-6520, 1991. The tissue pieces were minced into small (1 mm³) pieces and homogenized with a Teflon pestle on ice with 0.5% Triton X-100 in a solution containing 2 mM vanadyl ribonucleoside (RNase inhibitor) to release the lipids and soluble proteins. Extracts were then filtered through a 350 micron nylon mesh and extracted with 0.25 M ammonium sulfate to release the soluble cytoskeletal elements. DNase treatment at 25° C. was used to remove the soluble chromatin. The remaining fractions contained intermediate filaments and nuclear matrix proteins. This fraction was then disassembled with 8 M urea, and the insoluble components, which consisted principally of carbohydrates and extracellular matrix components, were pelleted. The urea was dialyzed out, and the intermediate filaments were allowed to reassemble and removed by centrifugation. The nuclear matrix proteins were then ethanol precipitated. All solutions contained freshly prepared 1 mM phenylmethylsulfonylfluoride (PMSF) to inhibit serine proteases, 0.3 µM aprotonin, 1 µM leupeptin and 1 µM pepstatin. Antibodies to proteins of this fraction were prepared and demonstrated to be localized exclusively in the nucleus and isolated nuclear matrix fraction. The protein composition was determined by resuspending the proteins in 0.1 N sodium hydroxide and utilizing the Coomassie Plus protein assay reagent kit (Pierce, Rockford, Ill.) with bovine serum albumin (BSA) as a standard.

For two-dimensional gel electrophoresis, the ethanol precipitated NMPs were dissolved in a sample buffer consisting of 9 M urea, 65 mM 3-[(3-Cholamidopropyl)-dimethyl-ammonio]-1-propanesulfonate (CHAPS), 2.2% ampholytes and 140 mM dithiothreitol. The final pellet containing NMPs represented less than 1% of the total cellular proteins.

High Resolution Two-Dimensional Electrophoresis

High resolution two-dimensional gel electrophoresis was carried out utilizing the Investigator 2-D gel system (Oxford Glycosystems, Bedford, Mass.). Briefly, one-dimensional isoelectric focusing was carried out for 18,000 V-h using 1-mm×18-cm tube gels after 1.5 h of prefocusing. The tube gels were extruded and placed on top of 1-mm sodium dodecyl sulfate Duracryl (Oxford Glycosystems, Bedford, Mass.) high tensile strength polyacrylamide electrophoresis slab gels, and the gels were electrophoresed with 12° C. constant temperature regulation for approximately 5 hours. Gels were fixed with 50% methanol and 10% acetic acid. After thorough rinsing and rehydration, gels were treated with 5% glutaraldehyde and 5 mM dithiothreitol after buffering with 50 mM phosphate (pH 7.2). The gels were stained with silver stain (Accurate Chemical Co., Inc., Westbury, N.Y.) or transferred to PVDF (Immobilon, Millipore Corporation) as follows. Fifty micrograms of nuclear matrix protein were loaded for each gel. Protein molecular weight standards were Silver Standards from Diversified Biotechnology (Newton Centre, Mass.). Isoelectric points were determined using carbamylated standards from Gallaro-Schlesiwger, Inc. (Carle Place, N.Y.) and Sigma Chemical Co. (St. Louis, Mo.). Multiple gels were run for each sample, and multiple samples run at different times. Only protein spots clearly and reproducibly observed in all the gels of a sample type were counted as actually representing the nuclear matrix components. The gels were analyzed using the BioImage Electrophoresis Analysis System (BioImage, Ann Arbor, Mich.) which matches protein spots between gels and databases the gels and protein spots.

Protein Sequencing

Following identification of the bladder cancer-associated nuclear structural proteins, the proteins were sequenced from spots isolated by two-dimensional gel electrophoresis. The proteins were isolated according to an adaptation of a technique developed by Gevaert et al., *New strategies in high sensitivity charaterization of proteins separated from* 1-D or 2-D, In M. Z. Atassi and E. Apella (eds.), *Methods in Protein Structure Analysis*, pp. 15-26, Plenum Press, New York, N.Y. (1995). The two-dimensional gels were negatively stained by incubation in 0.2 M imidazole for 15 min, washed several times with deionized water, and stained with warm 0.3 M zinc chloride. The staining was stopped with deionized water. The proteins of interest were removed from the gel and stored at −80° C. The proteins were pooled and concentrated into an agarose gel before sending for sequencing (Department of Biochemistry, Michigan State University, East Lansing, Mich.), as described in Brunagel et al., *Cancer Research.* 62:2437-2442 (2002).

Antibody Production

The sequences obtained were used to produce peptides designed for use in antibody production. The peptide sequences were modified to contain a terminal cystiene for coupling purposes. The peptide sequences were verified by mass spectroscopy and conjugated to keyhole limpet hemocyanin or bovine serum albumin. Two New Zealand White rabbits per antigen were immunized and antiserum collected. Antibodies were produced by Harlan Bioproducts for Science, Indianapolis, Ind.

Immunoblot Analysis

Ten µg of NMP samples suspended in 1×PBS were loaded and separated by 7.5% SDS-PAGE. Ten µl of Rainbow marker (Amersham Life Sciences, Arlington Heights, Ill.) were loaded in a separate lane. The proteins were transferred to a polyvinylidene difluoride membrane (Milipore, Bedford, Mass.) using a semi-dry transfer apparatus (Bio-Rad, Richmond, Calif.) The membranes were incubated overnight in PBS with 4% non-fat dry milk and 0.2% Tween-20. The membranes were incubated at room temperature with a 1:50 dilution of primary BLCA-1 antibody in PBS with 2% non-fat dry milk and 0.2% Tween-20 for 1 hr. Antibody incubation was followed by three 15 minute washes with 1×PBS and 0.2% Tween-20. Secondary antibody, donkey anti-rabbit IgG conjugated with horseradish peroxidase (Amersham Life Sciences), was incubated at room temperature for 1 hr at a 1:20,000 dilution. The membrane was washed again with PBS and 0.2% Tween-20. Detection was achieved using a chemiluminescence reaction using the ECL Immunoblot kit (Amersham Life Sciences).

Enzyme Linked Immunosorbant Assay (ELISA)

Urine samples were obtained from patients diagnosed with bladder cancer, from normal individuals who did not have any urological abnormalities, and from individuals with spinal cord injuries under IRB approved protocols. The cancer patients ages ranged from 41-86 and normal individuals ranged from 22-57. Thirteen of the normal patients were males and 13 were females. Twenty of the cancer patients were males, four were females, and three were unknown. Two of the tumor samples were grade 1, nine were grade 2, eight were grade 3, two were CIS, and six were unknown. One hundred µl of urine was loaded into a 96-well flat bottom plate and incubated overnight at room temperature. 0.5 µg Rabbit IgG and 1 ng BLCA-1 peptide was used as a positive control. The following day, the plates were rinsed with deionized water and blocked with bovine serum blocking agent for 30 min. The plates were rinsed again and incubated for 2 hr with anti-BLCA-1 antibody. Rabbit pre-immune serum was used as a negative control. Following three washes with deionized water, secondary antibody, goat-anti-rabbit conjugated with alkaline phosphatase (Kirkegaard & Perry Laboratories, Inc, Gaithersburg, Md.), at a dilution of 1:5,000 was incubated for 2 hrs at room temperature. Detection was accomplished using TMB Microwell Peroxidase Substrate (1-Component) (Kirkegaard & Perry Laboratories). Plates were read at 630 nm.

Serum samples also were obtained from bladder cancer patients and evaluated by ELISA.

Results

Bladder tumor tissue as well as tissue from normal adjacent areas of the bladder were obtained and nuclear matrix proteins were extracted. After two dimensional gel electrophoresis, six proteins were identified that were specifically expressed in the tumor tissue while three proteins were identified which are expressed in normal adjacent tissue but not tumor tissue. The following NMPs were identified:

TABLE I

Proteins Associated With Human Bladder Cancer

| Protein | Molecular Weight (kD) | pI |
|---|---|---|
| BLCA-1 | 72 | 7.70 |
| BLCA-2 | 40 | 7.50 |
| BLCA-3 | 39 | 6.27 |
| BLCA-4 | 37 | 6.24 |
| BLCA-5 | 29 | 5.80 |
| BLCA-6 | 22 | 8.00 |

TABLE II

Proteins Associated with Normal Human Bladder

| Protein | Molecular Weight (kD) | pI |
|---|---|---|
| BLNL-1 | 70 | 6.09 |
| BLNL-2 | 66 | 5.89 |
| BLNL-3 | 66 | 5.80 |

In addition, the following sequence data has been obtained: BLCA-1 includes the amino acid sequence LAKIVL (SEQ ID NO: 1). BLCA-4 includes the amino acid sequences EISQLNAG (SEQ ID NO: 2) and VYEDIMQK (SEQ ID NO: 3). BLCA-6 includes the amino acid sequence SLDLDLII-AEVK (SEQ ID NO: 4).

Likewise, spots corresponding to BLCA-1 were isolated from the gels and concentrated to obtain peptide sequence data corresponding to this protein. The peptide sequences as well as their BLAST matches, organism of origin, and amount of homology are described in Table III.

TABLE III

Amino acid sequence data obtained from high resolution two-dimensional gel electrophoresis of BLCA-1 spots

| SEQ ID NO | Amino Acid Sequence | Database Matches | Organism | Homology |
|---|---|---|---|---|
| 10 | (N)XLDQEVNT(E) | Similar to ribosomal protein L17 | *Rattus norvegicus* | 7/8 |
|  |  | Choline kinase GmCK2p-like protein | *Arabidopsis thalaiana* | 7/10 |
|  |  | Glucose-1-phosephate adenylyltransferase | *Haemophilus influenzae* | 6/7 |
| 6 | ALILELEIEN | Mitochondrial processing peptidase-beta | *Homo sapiens* | 7/7 |
| 11 | MKFEMEQYL(E) | RNA1 polyprotein | Tobacco ringspot virus | 8/10 |
|  |  | Keratin-9 | *Homo sapiens* | 7/8 |
|  |  | Ovariam tumor protein isoform | *Drosophila melanogaster* | 6/8 |
|  |  | Cag island protein | *Helicobacter pylori* | 6/10 |
| 8 | TYEEKINKQGK | Phosphoribosylformyl-glycinamidine synthetase | *Salmonella typhimurium* | 6/7 |
| 9 | WLLEGFRSRR | Cell division protein ftsJ | *Rickettsia prowazekii* | 6/7 |
|  |  | Similar to G protein-coupled receptor MRGX3 | *Homo sapiens* | 8/10 |
|  |  | RNA polymerase I transcription factor RRN3 | *Homo sapiens* | 7/8 |

According to an extensive analysis of the sequence data it appears that BLCA-1 is a novel protein. There are several potentially interesting motifs contained within the protein. Two peptides from these motifs, TYEEKINKQGK (SEQ ID NO: 8) and WLLEGFRSRR (SEQ ID NO: 9) were conjugated to carrier proteins and sent for antibody production. Two rabbits were inoculated with each peptide, and the antibodies were all screened with bladder tissue. The expression of BLCA-1, as evaluated by the anti-BLCA-1 antibodies, was first tested via immunoblot using nuclear matrix proteins extracted from human bladder tissue. BLCA-1 is detected in bladder tumor tissue, but is not recognized in normal adjacent tissue, or tissue from normal organ donors (FIG. 1). This expression pattern does not appear to be related to the age of the tumor patients, as the majority of the donor tissues tested were from individuals ranging in age from 53-69.

Figure 2:
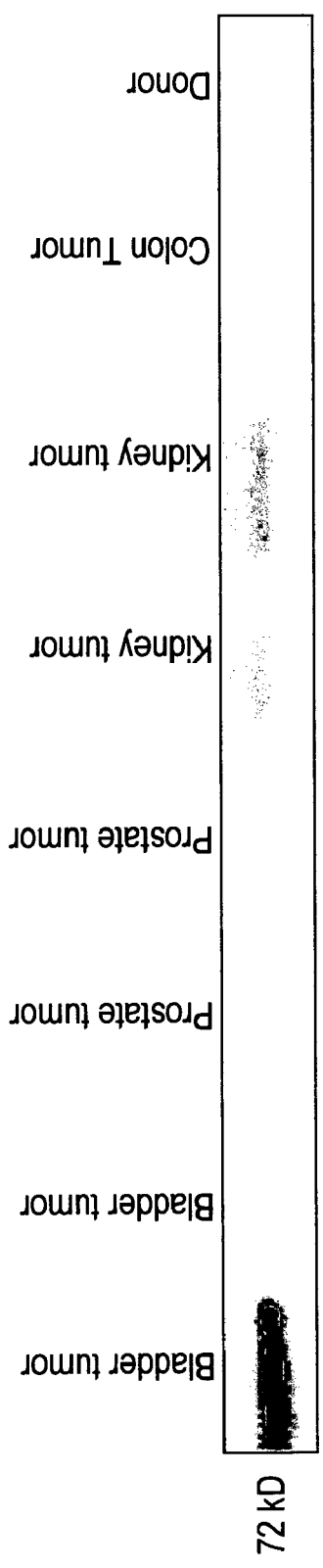
FIG. 2 shows an immunoblot of the nuclear matrix protein BLCA-1 in which an anti-BLCA-1 antibody was used to detect the protein in bladder tumor tissue as well as kidney tumor tissue but not in prostate tumor, colon tumor or donor tissue.

To further test the specificity of this antibody, nuclear matrix proteins from other tissue types were tested by immunoblot. BLCA-1 is not detected in prostate tumor tissue, colon tumor tissue, or normal organ donor tissue (FIG. 2). BLCA-1 was identified in extracts from renal tumor tissue. Detection of BLCA-1 in renal cell carcinoma may relate to the relationship in the urinary tract between the kidney and bladder.

Figure 3:
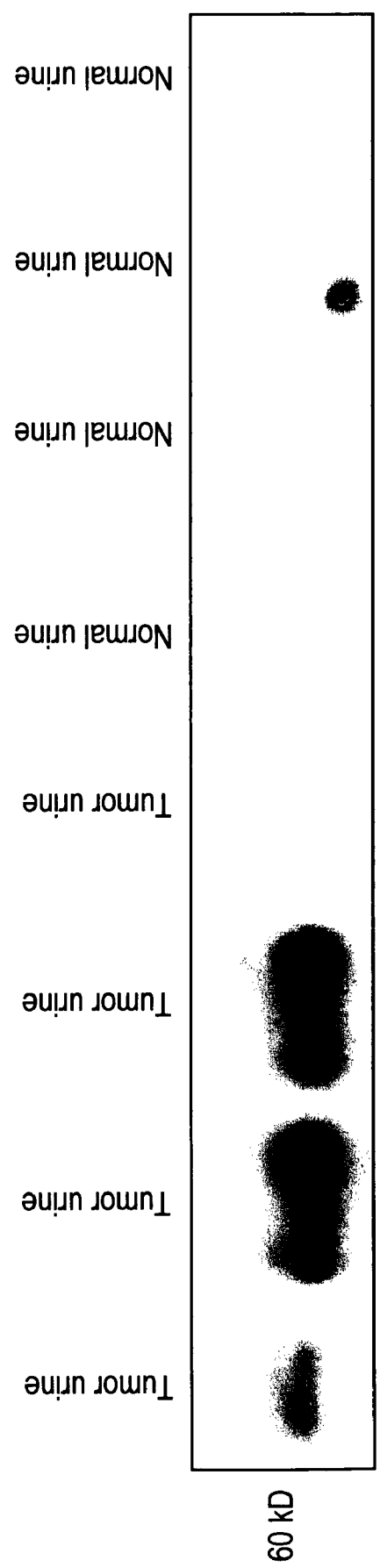
FIG. 3 shows an immunoblot of voided urine samples from subjects having bladder cancer and subjects without urologic malignancies.

Although the tissue staining patterns provide the scientific support for the use of this marker, the goal of these studies was to determine if indeed the marker could be detected in the urine. Utilizing the anti-BLCA-1 antibody, the protein is detected in the urine from individuals that have been diagnosed with bladder cancer, but is not expressed in the urine of normal individuals (FIG. 3). The protein appears to be slightly smaller in the urine than in the tissue, perhaps due to proteolytic cleavage in the acidic urine conditions.

In order to test for this protein in a more clinically applicable assay, we developed an ELISA, which can detect BLCA-1 specifically in the urine of bladder cancer patients. The antibody is able to detect small amounts (1 ng) of peptide prepared in a solution of PBS, and this is used in the assay as an additional positive control. After initial tests with urines from normal individuals and patients with bladder cancer, a cutoff absorbance value of 0.025 O.D. units was defined, with values less than this being considered normal and higher values would indicate bladder cancer. Subsequent tests were performed with 18 normal urine samples, 8 samples from individuals with spinal cord injuries, and 27 tumor urines. Spinal cord injury patients present a unique population in which to use in this assay because they have a high risk of bladder cancer and other urinary conditions such as chronic catheterization and cystitis. Traditional monitoring methods such as cytology are difficult to use in this population so a marker would be particularly useful to aid in bladder cancer diagnosis See, e.g., West et al., *Urology* 53:292-297 (1999) and Bejany et al., *J. Urol.* 138:1390-1392 (1987).

Figure 4:
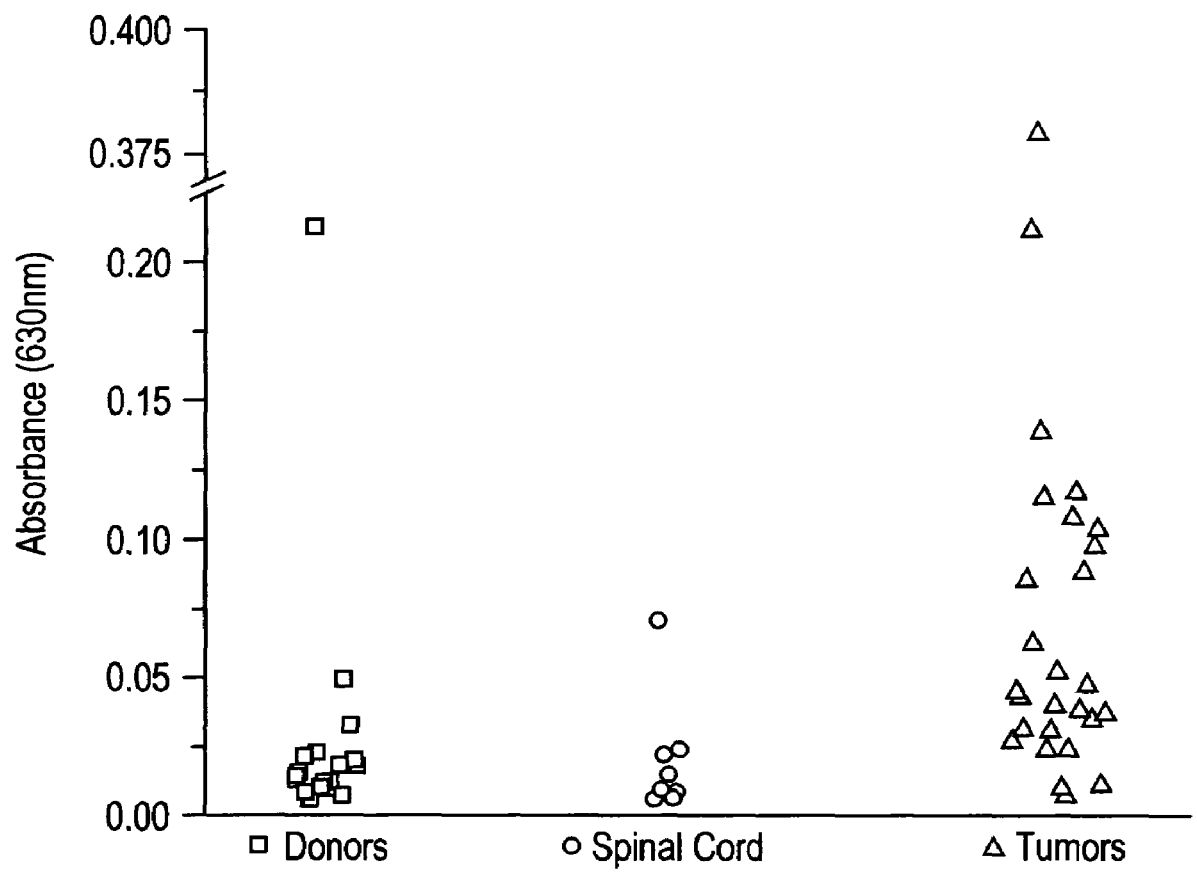
FIG. 4 shows that the nuclear matrix protein BLCA-1 is detectable in the urine of subjects having bladder cancer as compared to donors without urologic malignancies or subjects having spinal cord injuries.
Figure 5:
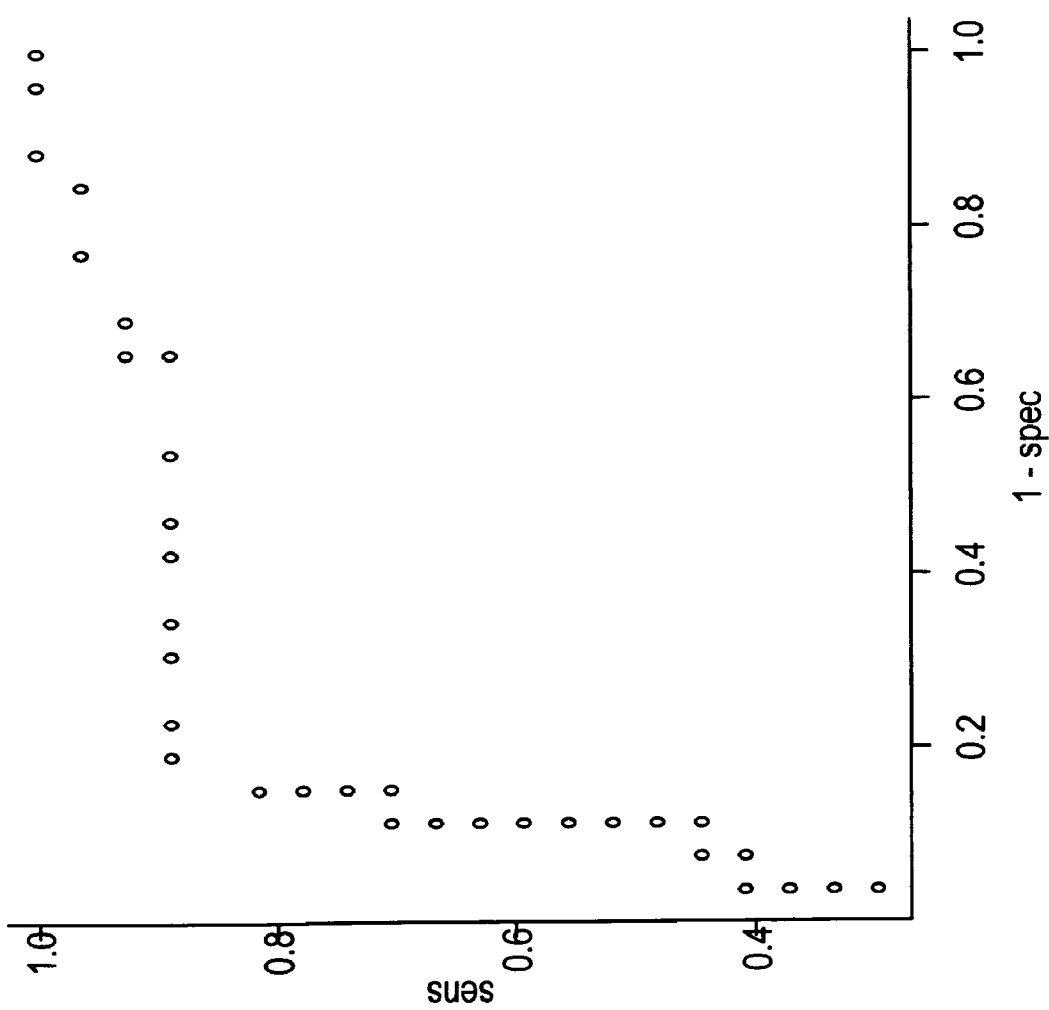
FIG. 5 shows a receiver operating characteristic (ROC) curve plotting the sensitivity by 1-specificity of a BLCA-1 urine-based immunoassay.

The average absorbance value for normal individuals was 0.028±0.047 with a median value of 0.015 O.D. units, while the average for patients with spinal cord injuries was 0.020±0.021 with a median value of 0.012 O.D. units. The average value for bladder cancer patients was 0.074±0.076, median value 0.045 O.D. units. The BLCA-1 protein levels in bladder cancer patients are significantly higher than the levels in normal individuals or those with spinal cord injuries (p-value 0.008 and 0.001 respectively). This assay is able to detect BLCA-1 levels above the cutoff in 22 out of 27 urine samples from patients with clinically diagnosed bladder cancer giving a sensitivity of 82% and only detected protein levels above the cutoff in 4 out of 26 normal individuals (normal and spinal cord injury patients combined) resulting in a specificity of 85% (FIG. 4). The sensitivity and specificity of the assay across various ranges of BLCA-1 measurements are shown (FIG. 5). This sensitivity and specificity is surprising and unexpected in view of the generally poor results of currently available assays utilizing samples of voided urine.

Figure 6:
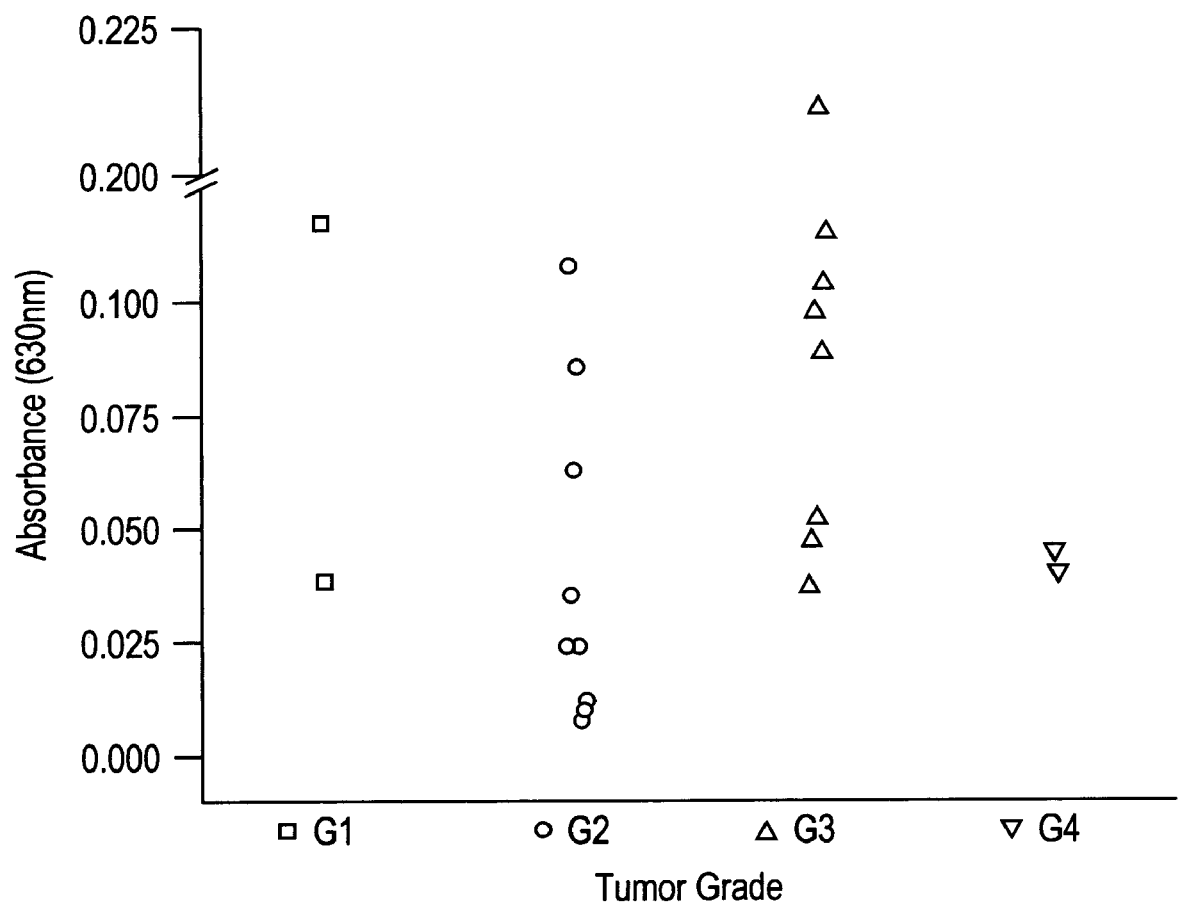
FIG. 6 shows the levels of BLCA-1 present in voided urine according to tumor grade.

In addition, there is a surprising and unexpected correlation between tumor grade and BLCA-1 expression (FIG. 6). There is a statistically significant difference between the absorbance values of grade 2 and grade 3 tumors (p-value 0.020). The average value for grade 2 tumors is 0.041 O.D. and for grade 3 tumors is 0.094 O.D.

Figure 7:
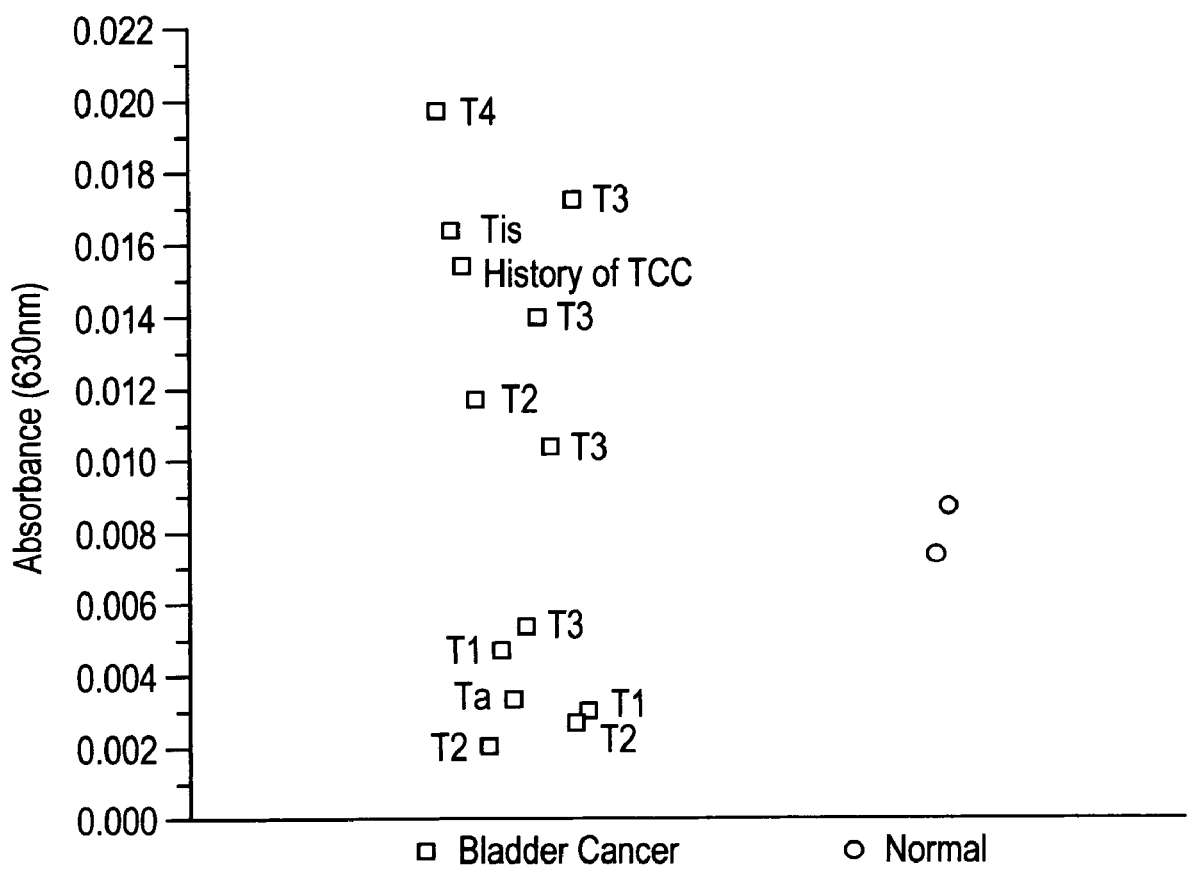
FIG. 7 shows the levels of BLCA-1 present in serum according to tumor grade.

ELISA also was performed on serum samples from bladder cancer patients, and an association between tumor stage and levels of BLCA-1 in patient serum was observed (FIG. 7).

Discussion

This research demonstrates that an antibody was successfully produced for the bladder cancer specific biomarker, BLCA-1. We show that this antibody can be used in immunoblots to selectively detect BLCA-1 both in tissue, serum and urine of bladder cancer patients, while the antibody does not detect the protein in tissue or urine samples collected from normal donors. Additionally, we have developed an immunoassay that can differentiate between urine samples from normal individuals and those with bladder cancer. Our assay has slightly lower specificity than cytology, the currently used detection method, but the sensitivity is much higher at 82%. Therefore, this assay may be clinically useful to increase the sensitivity of bladder cancer detection and as a result lead to increased survival of bladder cancer patients.

Another bladder cancer specific protein, BLCA-4, can also be selectively detected in tissue and urine from individuals with bladder cancer. See U.S. Pat. No. 5,866,535. While BLCA-1 is only detected in tumor tissue and not the normal adjacent or donor tissue, BLCA-4 is detected in both the tumor and normal adjacent tissue, suggesting this protein could be involved in a field effect for bladder cancer. An ELISA has been developed that can effectively differentiate between individuals with bladder cancer and individuals who do not have the disease with a sensitivity of 96.4% and a sensitivity of 100% 9. Earlier research on BLCA-4 has also demonstrated that the expression of this protein does not vary between bladder cancer stages or grades. Surprisingly, this study suggests that there is a correlation between the level of BLCA-1 expression and the tumor grade. In the future, animal studies, in which bladder cancer is induced, can be used to test how early this protein appears in bladder cancer progression and to verify the findings of this study.

This study has demonstrated that an antibody produced to the nuclear matrix protein BLCA-1 can selectively differentiate between both tissue and urine from individuals diagnosed with bladder cancer and normal donor patients. This protein is a urine-based marker of bladder cancer that could be used in conjunction with the already developed BLCA-4 urine-based ELISA assay or alone to enhance sensitivity and specificity of the detection of this disease.

While the invention is described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention. All references and publications cited herein are incorporated by reference in their entireties.

I claim:

1. An isolated or purified antibody that specifically binds to a fragment of a nuclear matrix protein, wherein said nuclear matrix protein is present in cancerous bladder cells but absent in normal bladder cells, wherein the nuclear matrix protein is BLCA-1 having a molecular weight of about 72 kD, as determined by SDS-PAGE, and a pI of about 7.70, and wherein the fragment consists of SEQ ID NO: 9.

2. The antibody of claim 1, wherein the antibody is selected from the group consisting of monoclonal antibody, polyclonal antibody, humanized antibody, and antigen binding fragment.

3. The antibody of claim 1, wherein the antibody is coupled to a therapeutic agent.

4. The antibody of claim 1, wherein the antibody is labeled with a labeling agent selected from the group consisting of a radioisotope or paramagnetic isotope, a bioluminenscent compound, a chemiluminescent compound, a fluorescent compound, a metal chelate, an enzyme, and biotin.

* * * * *